(12) United States Patent
Marshall et al.

(10) Patent No.: US 10,105,079 B2
(45) Date of Patent: Oct. 23, 2018

(54) LANCING DEVICE

(71) Applicant: OWEN MUMFORD LIMITED, Oxford, Oxfordshire (GB)

(72) Inventors: Jeremy Marshall, Oxford (GB); Timothy Evans, Oxfordshire (GB)

(73) Assignee: OWEN MUMFORD LIMITED, Oxford (GB)

( * ) Notice: Subject to any disclaimer, the term of this patent is extended or adjusted under 35 U.S.C. 154(b) by 971 days.

(21) Appl. No.: 14/374,796

(22) PCT Filed: Jan. 28, 2013

(86) PCT No.: PCT/GB2013/050179
§ 371 (c)(1),
(2) Date: Jul. 25, 2014

(87) PCT Pub. No.: WO2013/110953
PCT Pub. Date: Aug. 1, 2013

(65) Prior Publication Data
US 2015/0313513 A1 Nov. 5, 2015

Related U.S. Application Data

(60) Provisional application No. 61/591,465, filed on Jan. 27, 2012.

(30) Foreign Application Priority Data

Jan. 27, 2012 (GB) .................................. 1201417.1

(51) Int. Cl.
*A61B 17/32* (2006.01)
*A61B 5/15* (2006.01)
*A61B 5/151* (2006.01)

(52) U.S. Cl.
CPC ...... *A61B 5/1411* (2013.01); *A61B 5/150022* (2013.01); *A61B 5/150114* (2013.01);
(Continued)

(58) Field of Classification Search
CPC .............. A61B 5/1411; A61B 5/15194; A61B 5/15186; A61B 5/150511; A61B 5/15144;
(Continued)

(56) References Cited

U.S. PATENT DOCUMENTS 2,711,738 A 6/1955 Kelly et al.
2,823,677 A 2/1958 Hein, Jr.
(Continued)

FOREIGN PATENT DOCUMENTS

EP  0 747 006 A1  12/1996
EP  1 287 785 A   3/2003
(Continued)

OTHER PUBLICATIONS

GB Search Report, dated Sep. 13, 2012, from corresponding GB application.
(Continued)

*Primary Examiner* — Diane Yabut
*Assistant Examiner* — Erich Herbermann
(74) *Attorney, Agent, or Firm* — Young & Thompson

(57) ABSTRACT

A lancing device includes a lancet body (14) of elongate form and having a sharp tip (16) at the forward end thereof; a drive spring (26) for imparting generally longitudinal movement to the lancet body, and a housing (10) receiving the lancet body and having an aperture (22) in the forward end thereof through which the sharp tip (16) of the lancet body projects in use when the device is fired. The device includes elements (28, 30, 32) for controlling movement of
(Continued)

the lancet body (14) to cause the tip of the lancet to execute a lateral movement when it projects from the aperture.

18 Claims, 12 Drawing Sheets

(52) U.S. Cl.
CPC ...... *A61B 5/15117* (2013.01); *A61B 5/15128* (2013.01); *A61B 5/15144* (2013.01); *A61B 5/15186* (2013.01); *A61B 5/15194* (2013.01); *A61B 5/150282* (2013.01); *A61B 5/150458* (2013.01); *A61B 5/150465* (2013.01); *A61B 5/150511* (2013.01); *A61B 5/150916* (2013.01); *A61B 5/150259* (2013.01)

(58) Field of Classification Search
CPC ............ A61B 5/15128; A61B 5/15117; A61B 5/150458; A61B 5/150465; A61B 5/150282; A61B 5/150022; A61B 5/150114; A61B 5/150916; A61B 5/150259
USPC ......................................................... 606/181
See application file for complete search history.

(56) References Cited

U.S. PATENT DOCUMENTS

| | | | |
|---|---|---|---|
| 3,358,689 A | 12/1967 | Higgins | |
| 4,064,871 A | 12/1977 | Reno | |
| 4,157,086 A | 6/1979 | Maiorano et al. | |
| 4,643,189 A | 2/1987 | Mintz | |
| 4,712,548 A * | 12/1987 | Enstrom | A61B 5/15142 30/357 |
| 5,527,333 A | 6/1996 | Nikkels et al. | |
| 5,527,334 A | 6/1996 | Kanner et al. | |
| 5,545,174 A | 8/1996 | Schenk et al. | |
| 5,571,132 A | 11/1996 | Mawhirt et al. | |
| 6,589,261 B1 | 7/2003 | Abulhaj et al. | |
| 8,523,784 B2 | 9/2013 | Kuhr et al. | |
| 9,724,031 B2* | 8/2017 | Yi | A61B 5/150916 |
| 2003/0225429 A1 | 12/2003 | Garthe et al. | |
| 2006/0052809 A1 | 3/2006 | Karbowniczek et al. | |
| 2006/0106411 A1 | 5/2006 | Schraga | |
| 2007/0055297 A1 | 3/2007 | Fukuzawa et al. | |
| 2007/0095178 A1 | 5/2007 | Schraga | |
| 2007/0293882 A1 | 12/2007 | Harttig | |
| 2010/0063418 A1* | 3/2010 | Wessel | A61B 5/150022 600/583 |
| 2010/0168774 A1 | 7/2010 | Morita et al. | |
| 2011/0264131 A1* | 10/2011 | Sun | A61B 5/1411 606/182 |

FOREIGN PATENT DOCUMENTS

| | | |
|---|---|---|
| JP | 2010148694 A | 7/2010 |
| WO | 98/11821 A1 | 3/1998 |
| WO | 98/14125 A1 | 4/1998 |
| WO | 02/065910 A1 | 8/2002 |
| WO | 2005091878 A2 | 10/2005 |
| WO | 2006/110742 A2 | 10/2006 |
| WO | 2008/107382 A1 | 9/2008 |
| WO | 2009/103759 A1 | 8/2009 |
| WO | 2011/158669 A1 | 12/2011 |
| WO | 2012/050520 A1 | 4/2012 |

OTHER PUBLICATIONS

GB Search Report, dated Sep. 17, 2012, from corresponding GB application.
GB Search Report, dated May 22, 2012, from corresponding GB application.
International Search Report, dated May 21, 2013, from corresponding PCT application.

* cited by examiner

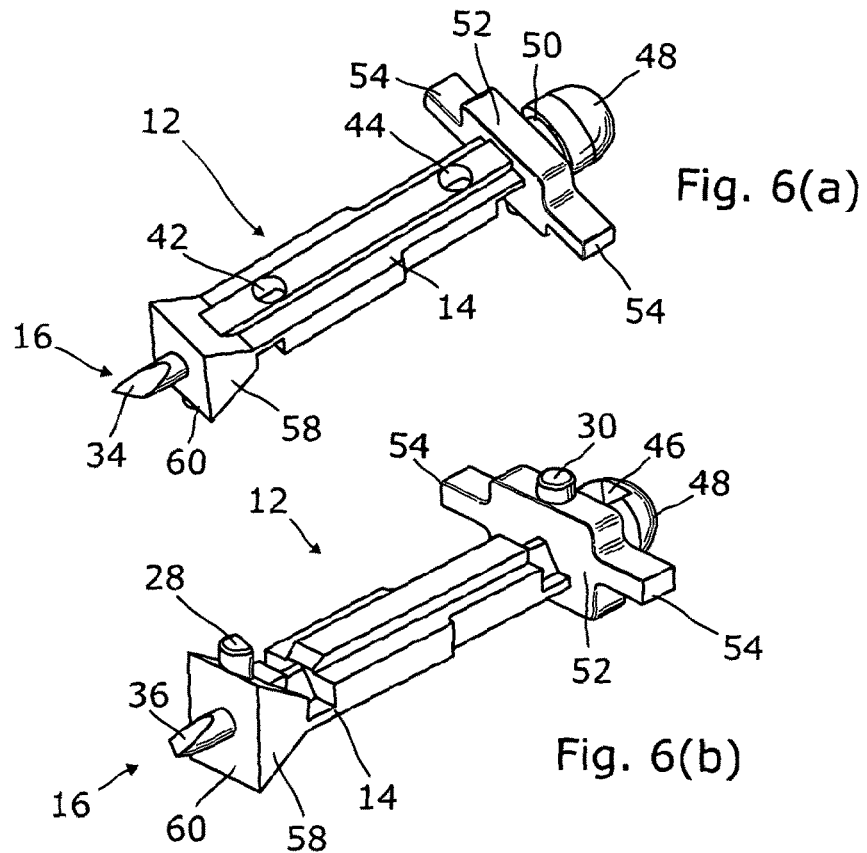
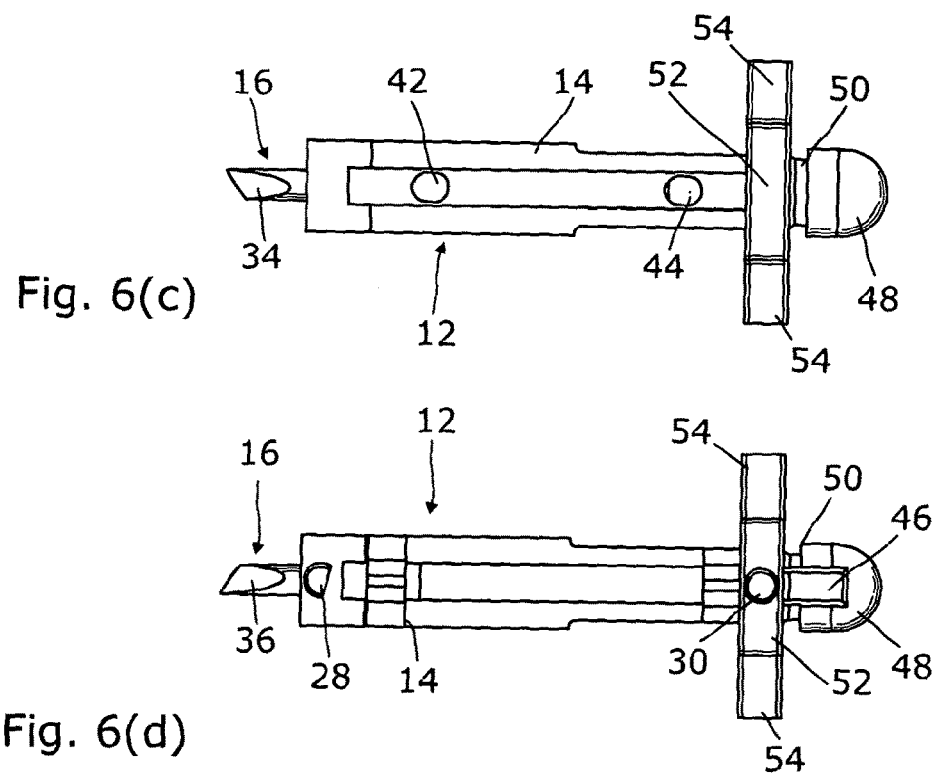

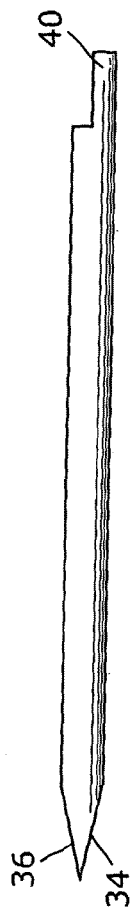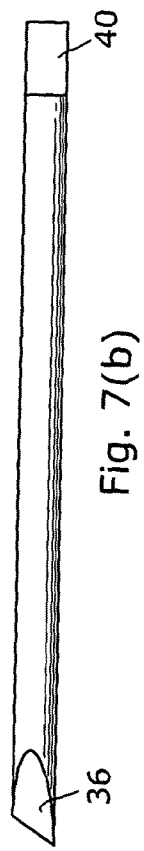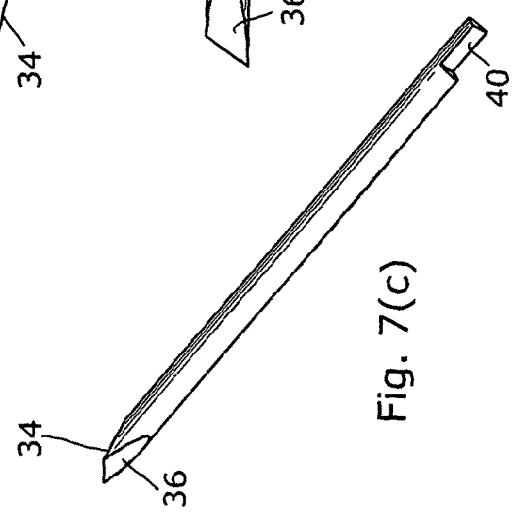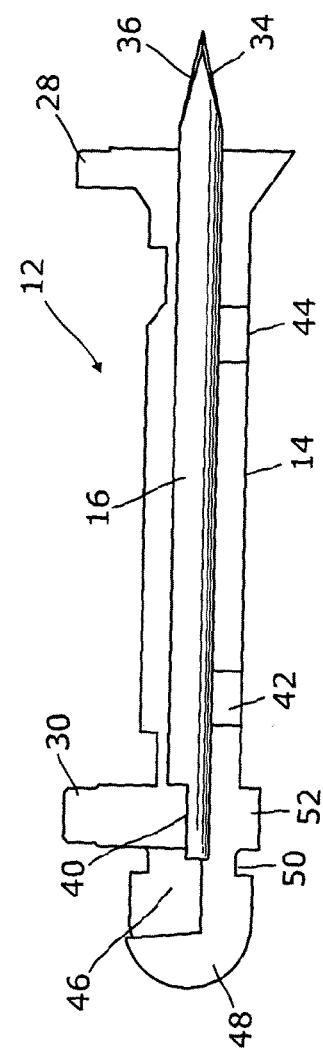

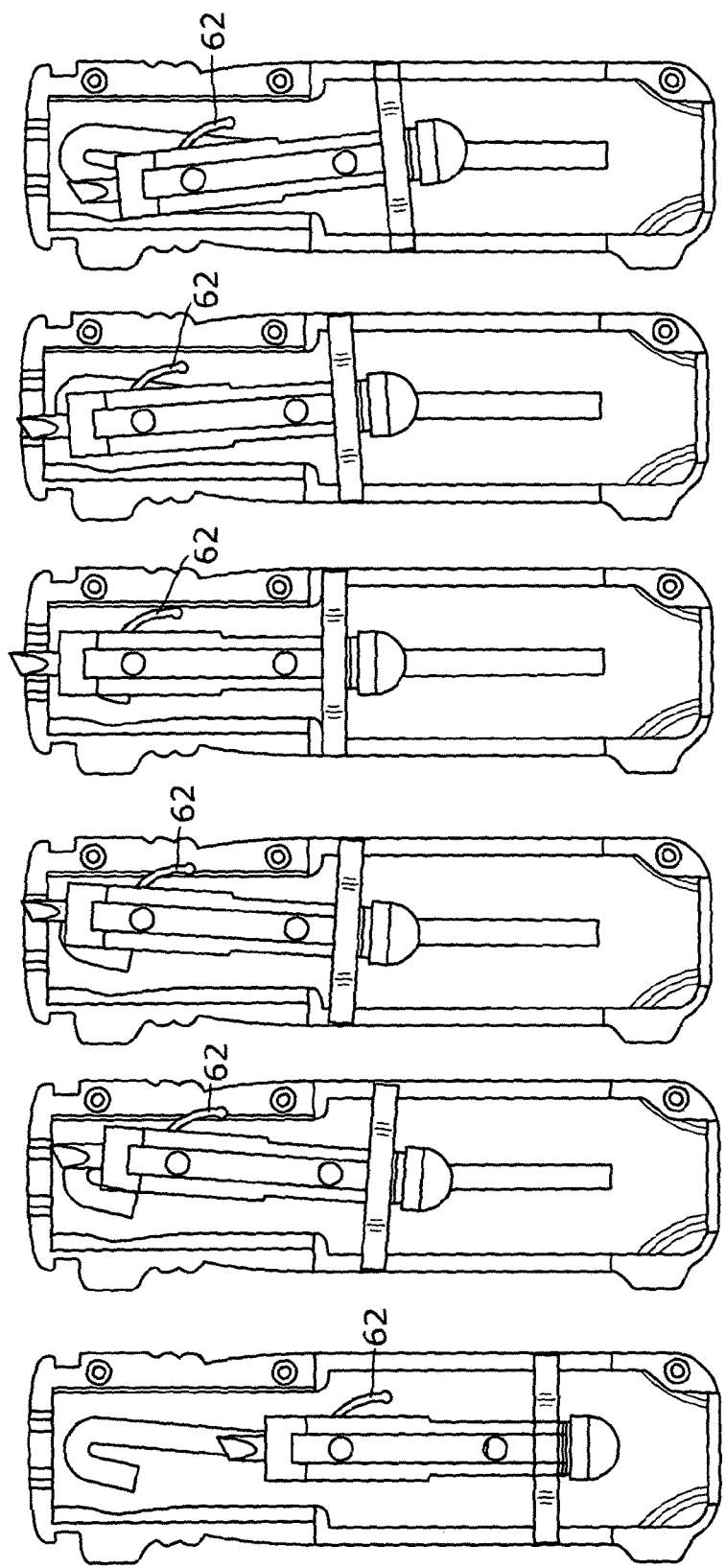

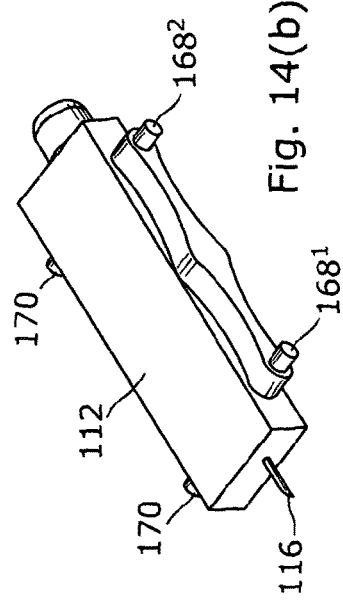
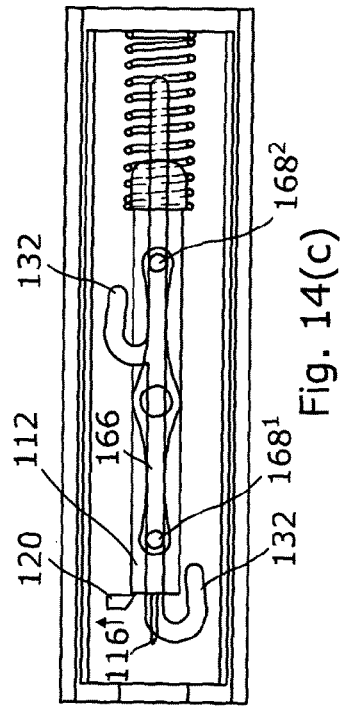
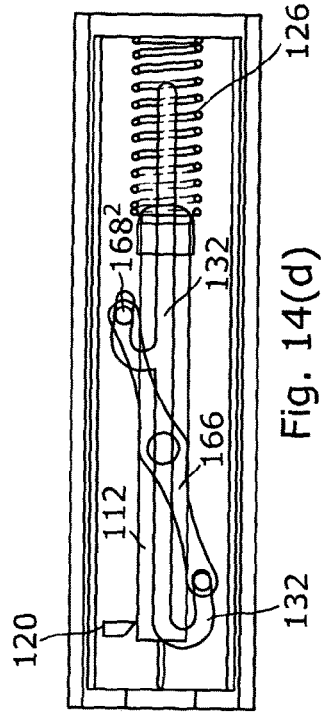
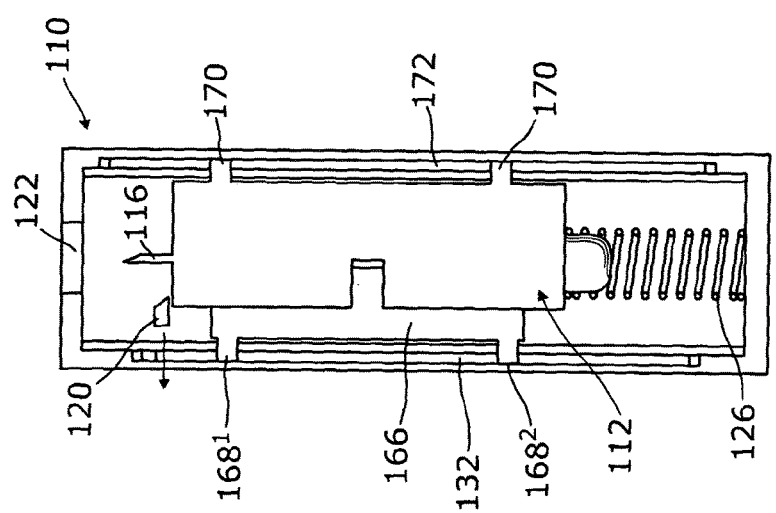

LANCING DEVICE

BACKGROUND OF THE INVENTION

Field of the Invention

This invention relates to lancing devices and in particular, but not exclusively, to such devices intended for single use. In many conventional lancing devices such as our Unistik® lancing device, a sharp-tipped lancet body of elongate form is contained within a housing and energised by a compression spring. The sharp tip is typically provided by the sharpened end of a lancet needle around which the lancet body is moulded. When fired, the lancet body executes a longitudinal extension and retraction movement to provide a linear pricking action. The linear action allows use of a linear acting spring and contributes to a device which is highly reliable. The longitudinal movement and consequent simplicity of action lead to a low component count, which facilitates manufacture and assembly. Also a low component count means lower accumulated tolerance which is important where dimensional accuracy is critical to ensure the lancet penetration is predictable and neither too deep nor too shallow.

In some situations, for example drawing a bead of blood from the heel of a neonate or where a greater volume of blood is required, a different lancing action may be called for. Instead of a linear pricking action a slicing action may be beneficial in order to sever the capillaries. There are therefore a number of designs of lancing devices that use a blade rather than a needle and which generally rotate the blade to cause the blade to pass through an aperture in a housing of the lancing device to slice the skin to produce a short slit or incision in the skin through which blood may pass to the skin surface. In the latter type of devices, the construction is generally more complex, making use of a blade rather than a needle, and they also typically employ a pivotal arrangement driven by a torsion spring to cause the blade to follow an arcuate path.

Description of the Related Art

U.S. Pat. No. 4,157,086 discloses an arrangement in which a torsion spring imparts rotary drive to a pin which causes a predetermined and repeatable movement of a blade.

U.S. Pat. No. 5,527,333 discloses an arrangement in which a user presses a trigger element which extends an initially unstressed spring to stretch it against its bias to extend a blade from a housing. Accordingly the blade is moved forwardly by the user pressing the trigger, and not by release of strain energy stored in the spring.

U.S. Pat. No. 2,823,677 discloses a device driven by a torsion spring.

US2007/0095178 discloses a device in which a blade is connected to a toggle linkage by a transversely acting spring. The device is fired by pressing on a trigger cap which biases and then releases the linkage.

U.S. Pat. No. 5,571,132 discloses an arrangement in which a blade is propelled forwardly along a predetermined path by a user applying an input force, and not by release of strain energy.

U.S. Pat. No. 4,643,189 discloses an arrangement in which a rotary or transversely acting spring drives a blade to effect an incision.

BRIEF SUMMARY OF THE INVENTION

We have designed a device which applies a slicing action to an implement with a cutting edge and which conveniently employs a longitudinally directed spring that is strained to apply a forward acting force on the lancet to drive it to effect an incision thereby enjoying many of the benefits of the first mentioned devices. It is a further aim of the invention to provide a device which achieves a slicing action by means of a modified needle profile.

Accordingly, in a first aspect, the invention provides a lancing device comprising:

a lancet body of elongate form and having a sharp tip at the forward end thereof;

a longitudinally acting drive spring for biasing said lancet body forwardly;

a housing receiving said lancet body and having an aperture in the forward end thereof through which the sharp tip of the lancet body projects in use when the device is fired;

wherein said device includes means for controlling movement of the lancet body to cause the tip of the lancet to execute a lateral movement when it projects from said aperture.

In another aspect, the invention provides lancing device comprising:

a housing with a lancing aperture at a forward end;

a lancet having a lancet body and a lancet tip at a forward end;

a longitudinally acting drive spring for biasing the lancet forwardly from a rearward, cocked position in which the tip is within said housing;

a trigger operable to hold said lancet in its rearward position against the spring bias but moveable to free said lancet for forward movement whereupon said drive spring moves said lancet forwardly to cause said tip momentarily to project from said housing and then rebounds to retract the tip back into the housing, and, cooperating surfaces associated with said housing and said lancet respectively for causing said tip to be deflected as said lancet moves forwardly, whereby said tip moves transversely as it projects through said lancing aperture.

It will be appreciated in this device that in the early stages of movement of preferred embodiments, a significant, if not major, component of movement of the lancet body is longitudinal, in a manner similar to linear lancing devices, and so allowing at least some of the design principles of these earlier devices to be utilised.

As in such earlier linear devices referred to, the drive force is preferably delivered by a linearly or longitudinally acting spring which is configured to release its strain energy to deliver a forward thrust to the lancet body. The thrust may be delivered by a spring acting in tension or compression, and any suitable configuration of spring may be used.

The means for controlling movement of the lancet body to cause lateral movement of the tip may take many forms. For example it may comprise cooperating control surfaces on the lancet body and the housing respectively. References to the housing include other elements attached or otherwise associated with the housing such as inserts or other components. The cooperating control surfaces may include a cam surface on the housing and a cam follower on the lancet body. Preferably, the lancet body includes a forward and a rearward cam follower, each of which cooperating with the cam surface throughout at least part of the forward stroke of movement of the lancet body when fired.

The cam surface may be profiled in various ways in order to achieve a lateral movement of the tip of the lancet when exposed. Thus the cam surface may include a generally longitudinal upstream portion and a curved or angled downstream portion adapted to cause said lateral movement when the tip is exposed. The upstream portion is preferably generally straight and parallel to the longitudinal axis of the device. The downstream portion may conveniently be arcuate or otherwise curved. The upstream portion may merge directly with the downstream portion but in a preferred arrangement an intermediate portion is provided which merges with the upstream and downstream portions. The intermediate portion is preferably inclined to the longitudinal axis so that the cam surface deviates firstly in one direction in the intermediate portion, and then in a reverse direction in the downstream portion so that correspondingly the lancet body tip moves transversely in one direction as it moves forwardly within the lancet housing before moving sharply in an opposite transverse direction when the tip is exposed through the aperture of the housing.

The upstream, intermediate and downstream portions may comprise one continuously curved portion, or one or more straight portions angled with respect to each other. The portions may be continuous or discontinuous. Alternatively, there may be a surface associated with the lancet and a surface associated with the body which interact only towards the end of the forward stroke of the lancet, to deflect the tip transversely.

Preferably the lancing device is designed so that, when fired, the drive spring urges the lancet body forwards to cause the tip to project through the housing aperture and then to retract back into the housing as the spring rebounds, retracting the lancet body with it, thereby to render the device safe. Where this is the case, the downstream portion is preferably generally U-shaped, with one limb of the U merging with the upstream portion or intermediate portion, as the case may be, whereby when the device is fired, the forward cam follower is driven down said one limb to the base of the U as the lancet body is driven forwardly by the spring and then backwardly along the other limb of the U when the lancet body is retracted by rebound action of the spring.

As previously, the outward and return portions of the U may be continuous or spaced from each other. Still further, instead of a U-shape, the track may simply be a return limb, which captures the cam follower as the lancet moves rearwardly on the rebound having momentarily projected the tip. Preferably, the other end of the limb of the U-shaped downstream portion, or the return limb, is blind or has an associated stop surface whereby, following firing, the lancet body is trapped against further rearward movement. This provides an irreversible action, thereby foiling attempts to recock the device by pushing the lancet body rearwards. Alternatively, the cooperating surfaces on or associated with the lancet body and the housing may define predetermined outward and return paths for the forward part of the lancet body as the drive spring initially drives the lancet body forward and thereafter rebounds.

The drive spring may be a compression or tension spring, and the device may be supplied with the spring pre-strained, or the user may be required initially to strain the spring before use. In preferred embodiments, the strain energy of the spring is the sole motive force acting on the lancet when fired.

The lancet body may be rigid along its length but, particularly where an extended incision arc is required, the lancet body may comprise articulated front and rear portions, with the rear portion constrained to follow a generally longitudinal path down the housing, whilst the forward portion is pivotally or flexibly attached to the rear portion and is provided with a guide peg that follows the profiled track. This means that, in use, the tip of the lancet follows an arc of tighter radius as the radius is defined by the distance between the tip and the articulation point, rather than by the spacing of the front and rear guide pegs of the illustrated embodiment.

Preferably, the lancet body has a further guide element running in a slot or groove in the housing to guide movement thereof.

The sharp tip of the lancet may take many forms. It could be a cutting edge forming part of the lancet body or it could be a cutting edge on an insert. Preferably the sharp tip of the lancet body is provided by the sharp forward end of a lancet needle forming part of the lancet body e.g. by the body being moulded around the needle. The needle is conveniently of cylindrical form having two machined surfaces defining a cutting edge at its forward end. The machined surfaces are preferably planar, provided by grinding or a similar operation. The angle between the faces defining the cutting edge is preferably in the range of from 20° to 40°. The cutting edge is preferably linear and preferably extends at an angle of between 30° and 80° to the longitudinal axis of the needle. This ensures that a knife edge is presented to the skin to provide an effective slicing action.

In order to facilitate manufacture and assembly of the device, the lancet needle is preferably provided with a datum feature spaced rearwardly of the tip. The datum feature may be used to ensure that the device is assembled with the needle angularly aligned so that the cutting edge of the needle moves in a single plane during the slicing action. It will be appreciated that it is important to ensure such angular alignment, and that a generally cylindrical needle will otherwise have no means of angular registration apart from the ground faces on the needle tip. The datum feature may take many forms but conveniently is a flat surface formed in the circumference of a rear end portion e.g. by removing a sector shape by grinding.

In another aspect this invention provides a lancet needle for being moved transversely to effect an incision in use, the needle being of cylindrical form including two machined surfaces defining a cutting edge at its forward end, and provided with a datum feature spaced rearwardly of the forward end.

In another aspect this invention provides a lancing device comprising:

a lancet body of elongate form and having a sharp tip at the forward end thereof;

a drive spring for imparting generally longitudinal movement to said lancet body from a cocked towards a fired position and thereafter retracting said lancet;

a housing receiving said lancet body and having an aperture in the forward end thereof through which the sharp tip of the lancet body momentarily projects in use when the device is fired;

wherein said device includes anti-recocking means for preventing return of the lancet body to the cocked position after having been fired, said anti-recocking means comprising a track with a return portion provided in or on said housing or lancet body, and a track follower element provided on the other thereof, wherein in use when the lancet has reached its forwardmost position, and as the lancet retracts, the track follower passes along the return portion and further retraction movement of the lancet is limited by interaction of the track and track follower.

Whilst the invention has been described above it extends to any inventive combination or sub-combination of the features set out above.

BRIEF DESCRIPTION OF THE DRAWINGS

The invention may be performed in various ways, and, by way of example only, one specific embodiment will now described in detail, reference made to the accompanying drawings in which:

FIGS. 6(a) to (d) are respective upper and lower perspective views and upper and lower plan views of the lancet used in the embodiment of FIGS. 1 to 5;

FIGS. 7(a) to (c) are side, bottom plan and perspective views respectively of a lancet needle used in the embodiment of FIGS. 1 to 6;

FIG. 8 is a sectional view through the lancet;

FIGS. 10(a) to (f) are views similar to those of FIGS. 9(a) to (f) but of a modified embodiment of device with a lancet body having a sprung side spur;

FIGS. 14(a) to (d) are views of another embodiment of a lancing device with a linear lancing action but cooperating with a branched profiled track to prevent recocking once used;

DETAILED DESCRIPTION OF THE PREFERRED EMBODIMENTS

Figure 4:
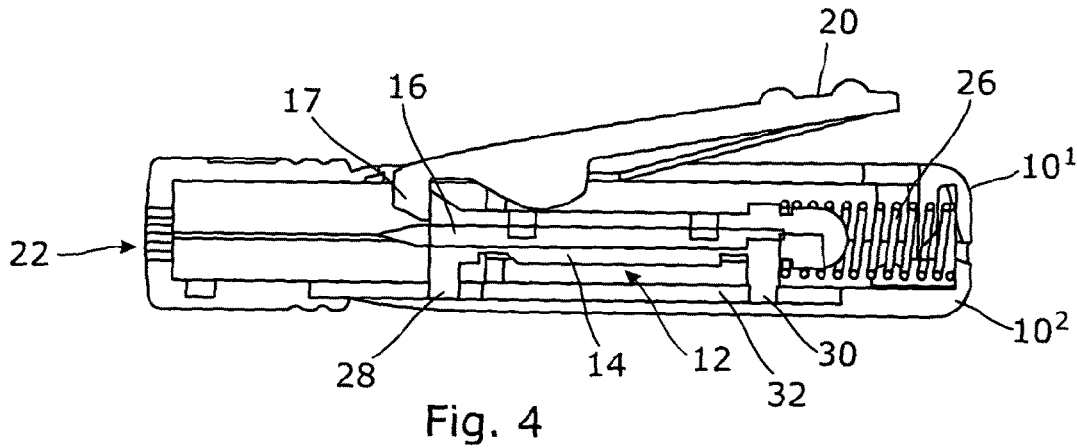
FIG. 4 is a cross-sectional view through the device.

Referring to the Figures, there are shown embodiments of lancing device comprising a housing 10 having upper and lower parts $10^1$ and $10^2$ respectively, and containing a lancet 12 made up of a lancet body 14 moulded around a sharpened lancet needle 16 as seen in FIGS. 6 to 8 below. The lancet 12 is held in a retracted position by means of a latch 17 on the forward end of a trigger lever 18 mounted as a rocker on the housing 10 by means of live hinges 19 and carrying a firing pad 20 at its rear end (as seen in FIG. 4). It will be appreciated that the cutting edge provided by the needle could instead be any other suitable cutting edge formed on an insert, or directly as an integral part of the lancet body. The element on which the cutting edge is formed may of any suitable material including metals and various plastics.

The front end wall of the housing 10 is provided with an elongate needle slot 22 through which the needle 16 of the lancet projects in use. Spaced around the lancet slot 22 on the front end wall of the housing are ten projections 24 which, when the device is applied to skin prior to firing, provide a distracting or confusing effect to remove or reduce the sensation of pain when the device is fired. The lancet 12 is urged forwardly by means of a spring 26 acting between the rear end of the lancet and an inner end wall of the housing 10 as seen in FIG. 4. In other views, the spring has been removed for clarity. The device may be supplied in a cocked condition with the lancet held in the position of FIG. 4 against the force of the spring by the trigger latch, or the device may be supplied in an uncocked position with provision for the user to cock the device by urging the lancet rearwardly against the power of the spring until it latches behind the trigger latch.

Figure 5A:
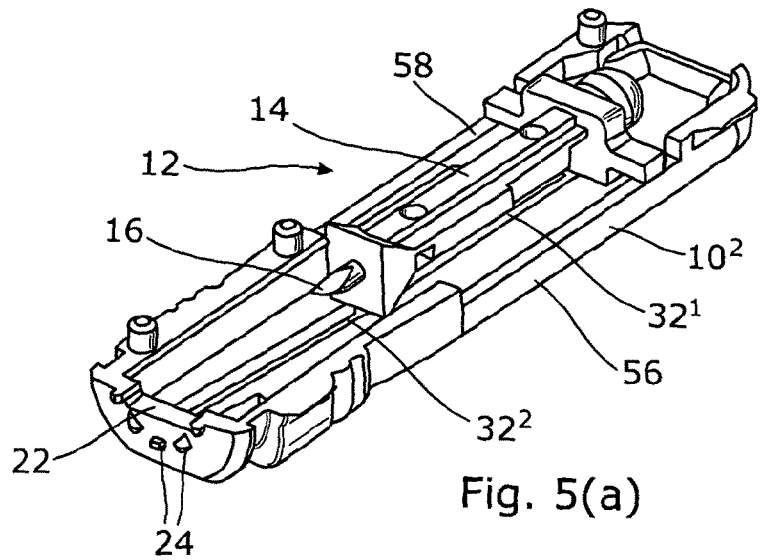
FIGS. 5(a) and (b) are perspective views of the lancet body engaged in the lower half of the housing with the upper half of the housing removed, viewed from different angles.
Figure 5B:
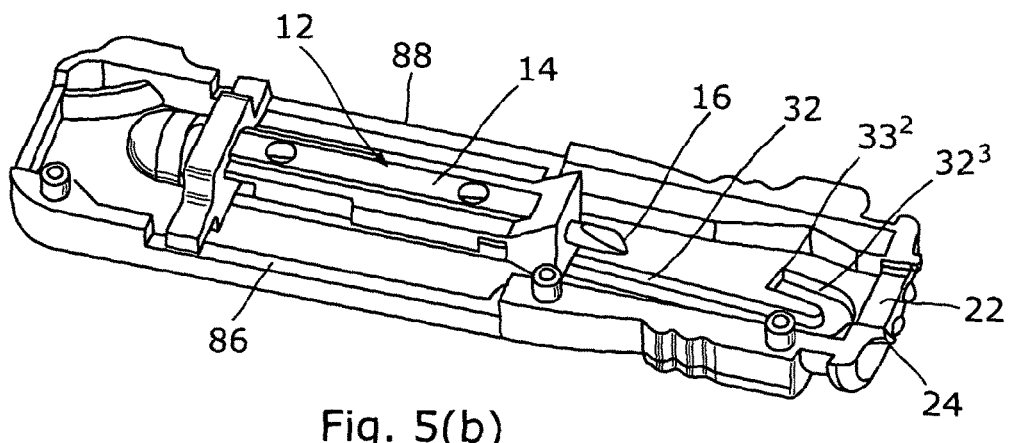
Figures 9A, 9B, 9C, 9D, 9E, 9F:
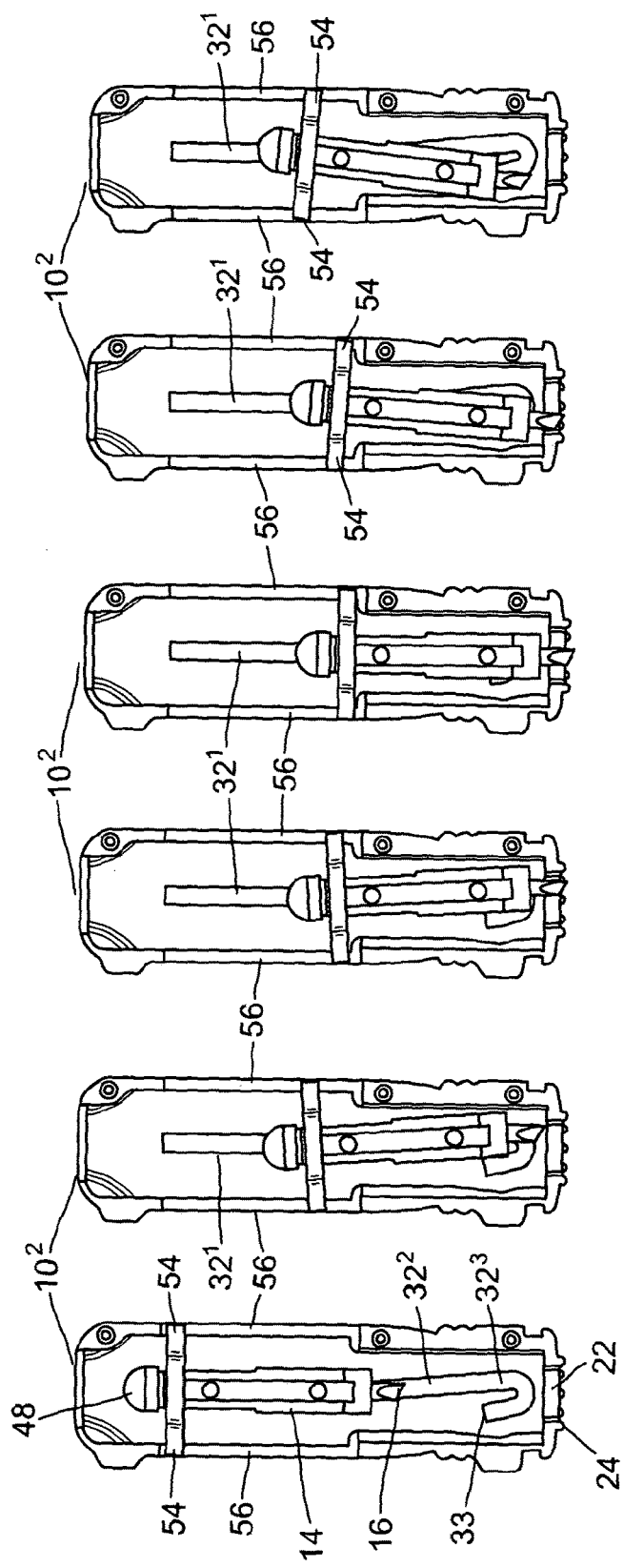
FIGS. 9(a) to (f) are respective views of the device with the upper housing part removed showing the sequence of movement of the lancet as it extends down the housing, projects and moves laterally to make an incision and then retracts, when the device is fired.

In many conventional devices, the lancet 12 executes a purely longitudinal movement when fired, to provide a puncture site in a stabbing action. In embodiments disclosed herein, the movement of the lancet 12 is controlled so that the lancet tip executes a transverse movement as it projects through the lancet slot 22 in the housing, thereby to make a short incision in the flesh as opposed to a puncture wound. In order to do this, the lancet 12 is provided with a forward and a rearward guide peg 28, 30 respectively on its underside (see FIG. 6(b)). These guide pegs run in a profiled track 32 or groove formed in the inner wall of the lower housing part 102, as seen in FIGS. 5 and 9. The track 32 is of generally cranked J-shaped form made up of a rearward longitudinal section $32^1$ coincident with the longitudinal axis of the device, an inclined portion $32^2$ which deviates to one side of the device (the right hand as seen in FIG. 9(a)), and finally a U-shaped portion $32^3$. The free end 33 of the U-shaped portion is blind. The guide pegs 28, 30 slide in the track 32, whilst the lancet 12 moves generally longitudinally down the body under the influence of the drive spring 26. The arrangement imposes a gentle angular movement to pivot the forward end of the lancet in one direction as it passes from the position shown in FIG. 9(a) to that shown in FIG. 9(b) before imposing an opposite sharp angular movement in the opposite direction as seen in FIGS. 9(c) to 9(e) as the tip of the lancet needle 16 is exposed through the lancet slot.

The drive spring 26 is designed so that, when fired, it initially overshoots its rest position to drive the lancet to the position shown in FIG. 9(d) before rebounding to pull the lancet past its apogee of movement and to retract it safely into the housing as shown in FIG. 9(f). In the position shown in FIG. 9(f) the engagement of the forward peg 28 with the blind end 33 of the U-portion of the track ensures that the device cannot be re-cocked by applying rearward pressure to the lancet through the lancing slot. The peg 28 may be flattened to make surface to surface contact with a flat surface at the blind end 33 of the track.

The embodiments of this invention ensure that the lancet needle presents a cutting edge 38 to cause an incision when the tip of the lancet needle exits the lancing slot. The tip of the lancing needle 16 is provided with two facets 34, 36 or faces that define the cutting edge 38. The planes defined by the faces intersect at an angle of typically 30° as seen in FIG. 7(a) although other angles may be selected according to the particular application. In addition, the cutting edge 38 (i.e. the line of intersection of the two planes) is inclined to the longitudinal axis so that the edge acts like a knife. The edge may typically lie at an angle of 60° to the longitudinal axis of the needle, as seen in FIG. 7(b).

The production of the lancing needle 16 requires precision grinding of the needle in a jig to provide the flats 34 and 36. During manufacture, typically a batch of needles are held in a jig and the two faces ground on the needles. It is important to ensure that the needles once produced are properly aligned when installed in the lancing device, such that the cutting edge 38 moves in a single plane as the needle tip exits the lancing slot of the housing and moves transversely. Any angular misalignment could adversely affect operation of the device leading to an ineffective or painful incision. In the disclosed embodiments, the lancing needles 16 are therefore initially provided with a datum flat 40 which is ground on the rear end of the needle. The datum flat 40 can be used to align the needles prior to grinding and therefore to ensure that the ground faces are in the same registration with respect to the ground flat 40. The flat 40 is used to align the needle in a unique correct angular orientation in the mould tool (not shown) which is used to mould the lancet body 14 around the lancet needle 16. The needle 16 may therefore initially be located in the mould by three pins, two of which exit the mould after formation of the lancet body from bores 42 and 44 as seen in FIG. 8, with the third pin contacting the datum flat 40 and holding the pin against rearward movement during the plastics moulding process and then exiting the mould to leave the recess 46 seen in FIG. 8.

Figure 1:
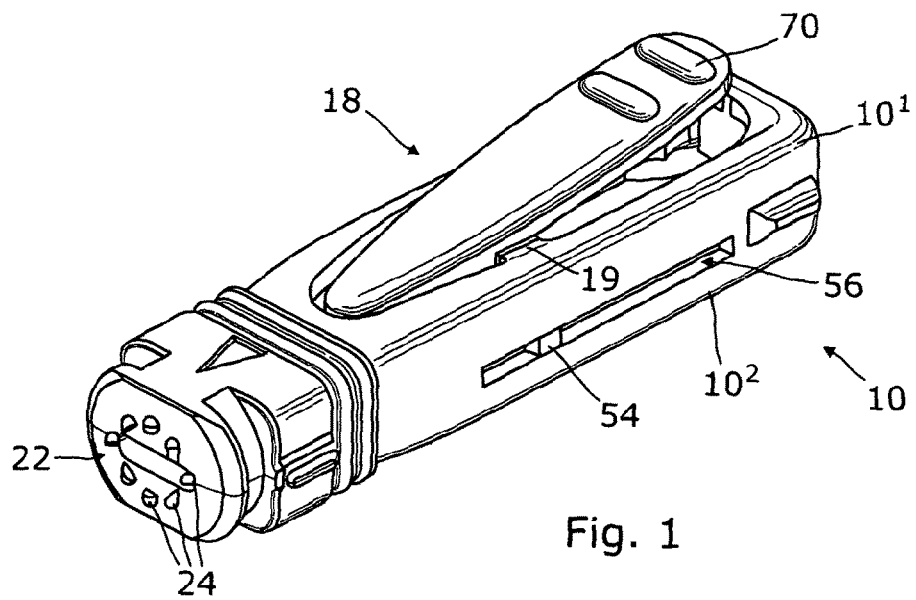
FIGS. 1, 2 and 3 are perspective, end and side views respectively of an embodiment of lancing device in accordance with this invention.
Figure 2:
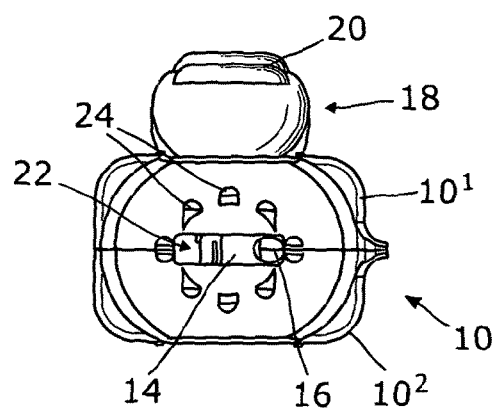
Figure 3:
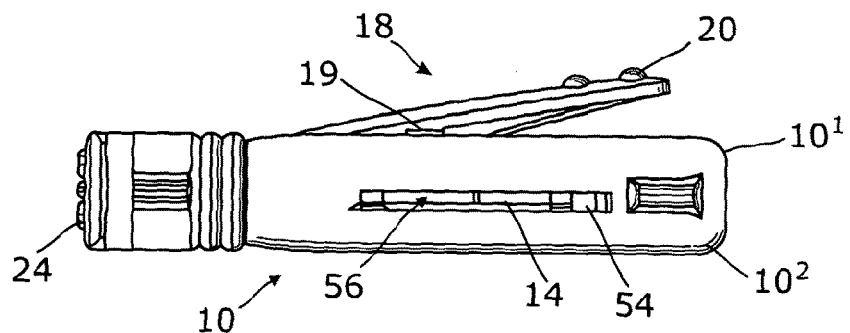

Referring now in more detail to FIG. 6, the lancet body includes at its rear end a bulbous spring retaining head 48 which is necked at 50 before merging with a generally rectangular flange 52 on the underside of which is formed the rearward peg 30. A pair of lateral guide stubs 54 project from either side of the flange and run in respective guide slots 56 in the side wall of the housing 10 (as seen in FIGS. 1 and 3). The guide stubs 54 stabilise movement of the rear end of the lancet 12 as its front end executes the lateral movements referred to above. The front guide peg 28 is integrally formed rear of the front edge of a generally trapezoidal formation 58 at the front end of the body, the front edge acting as a latch face 60 for the trigger latch 17.

Figure 11:
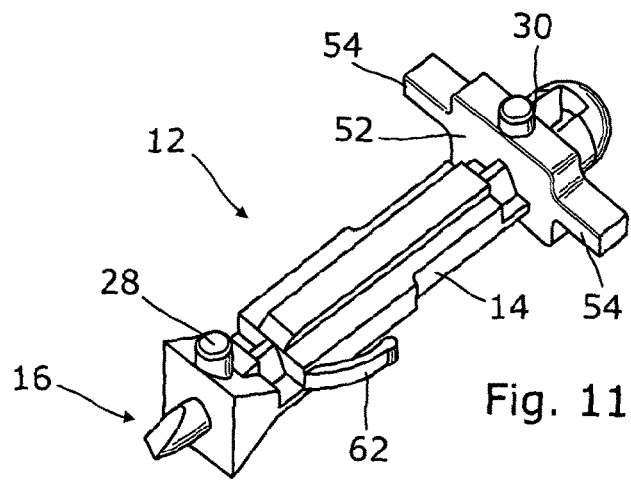
FIG. 11 is a view of the lancet body with a sprung side spur used in the embodiment of FIGS. 10(a) to (f)

As illustrated in FIGS. 10 and 11, in order to help movement of the lancet in the transverse direction as the forward peg moves around the U-shaped downstream portion $32^3$ of the track 32, the lancet body may be provided with a resilient spur 62 which compresses as the forward end of the lancet moves off axis from the positions of FIGS. 9(a) to 9(c), and then expands to urge the forward end in the opposite direction to help the forward peg 28 around the curved region of the U-shaped portion.

Figure 12:
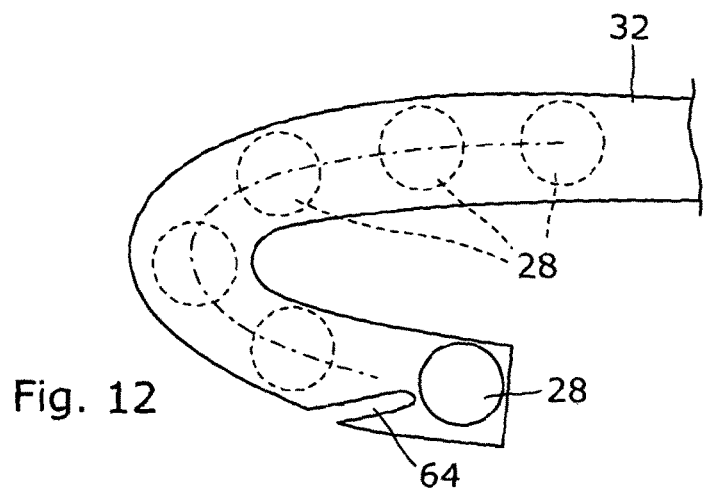
FIG. 12 is a view of a modification of the lancet guide track in the above embodiments to provide a snap-action non-return feature.

Referring to FIG. 12 if required, a non-return feature may be provided that traps the lancet against forward movement from the post-firing position (the position of FIGS. 9(f) and 10(f)). This could be by interaction of the lancet body and the housing. For example, as shown in FIG. 12 the track 32 may have a ramp or resilient latch portion 64 past which the forward peg 28 snaps as it approaches the blind end 33 of the downstream portion $32^3$ so that, after completion of a lancing operation the lancet is trapped against forward movement.

Figure 13:
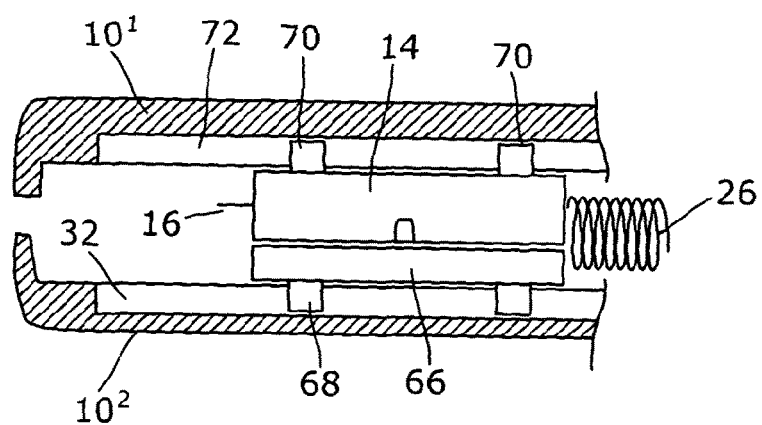
FIG. 13 is a schematic view of an embodiment of lancing device with a linear lancing action but cooperating with a J-shaped track to prevent re-cocking once used.
Figure 15B:
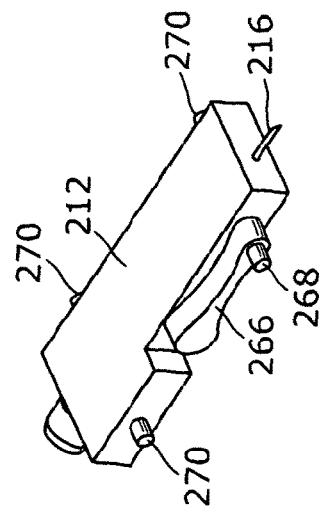
FIGS. 15(a) to (e) are views of a yet further embodiment of lancing device with a linear lancing action cooperating with a J shaped track to prevent recocking once used.
Figure 15C:
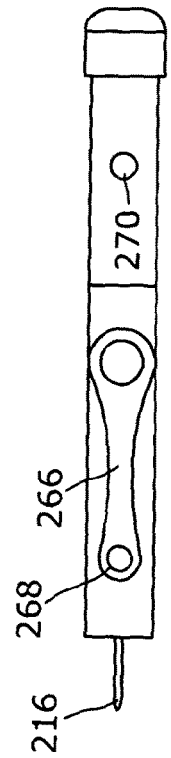
Figure 15A:
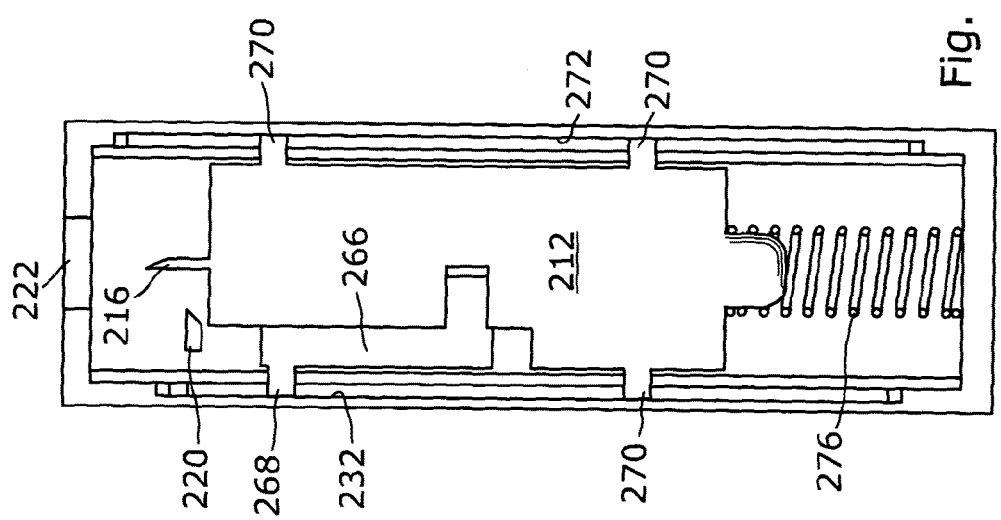
Figure 15D:
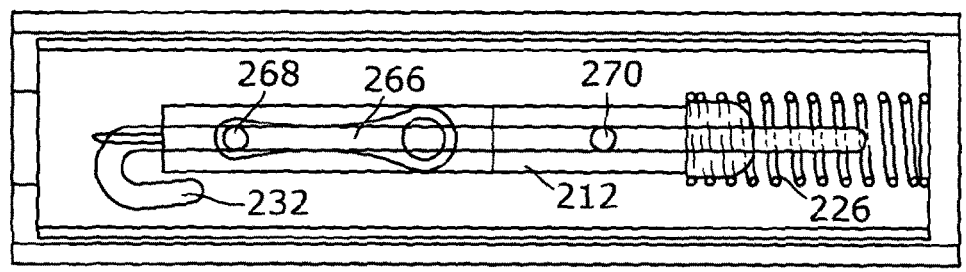
Figure 15E:
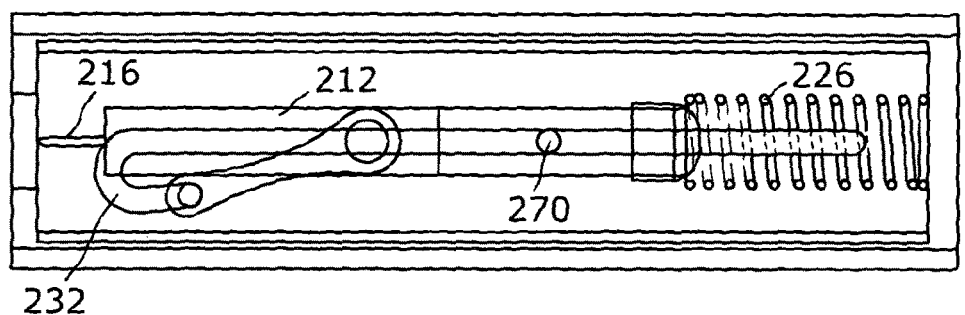
Figure 16A:
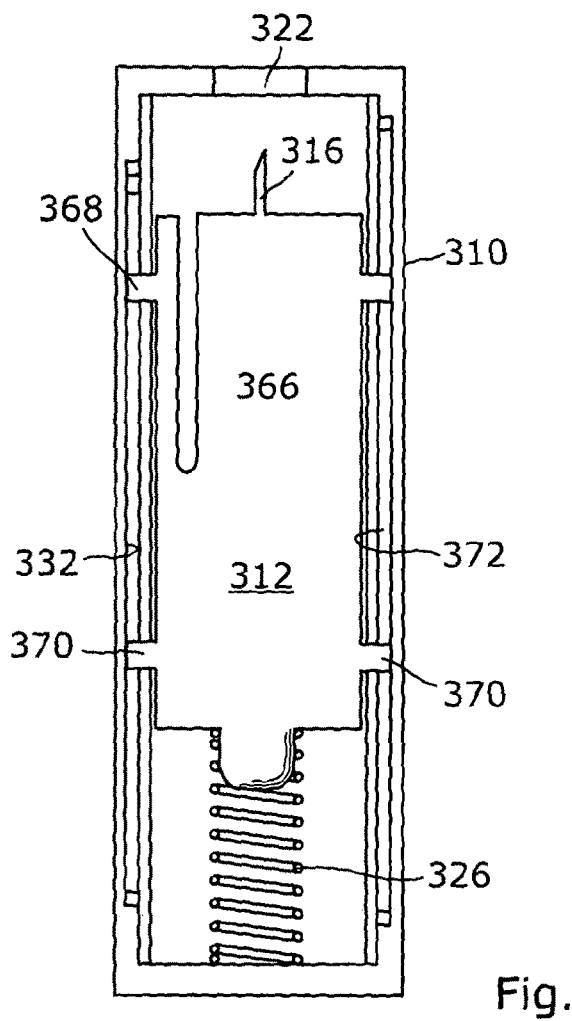
FIGS. 16(a) to (d) are views of a further embodiment of lancing device with a linear lancing action but cooperating with a J-shaped track to prevent recocking once used.
Figure 16B:
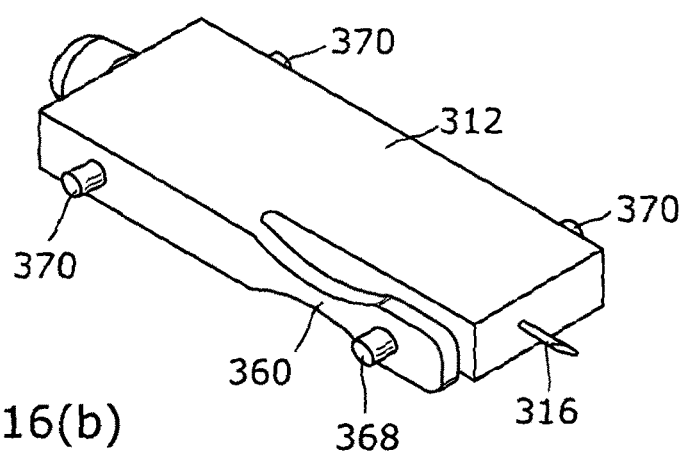
Figure 16C:
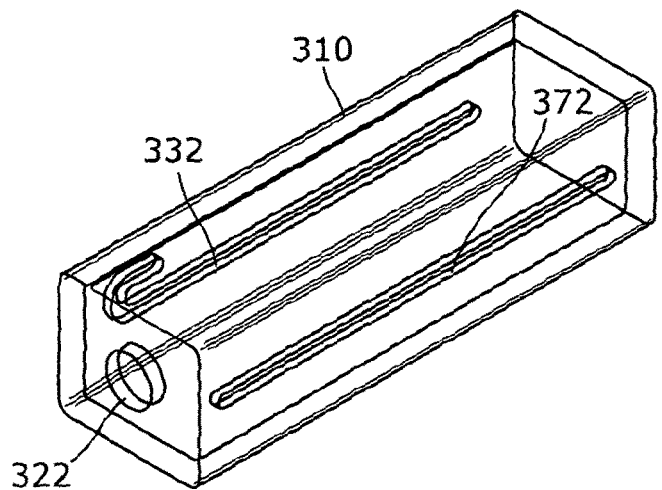
Figure 16D:
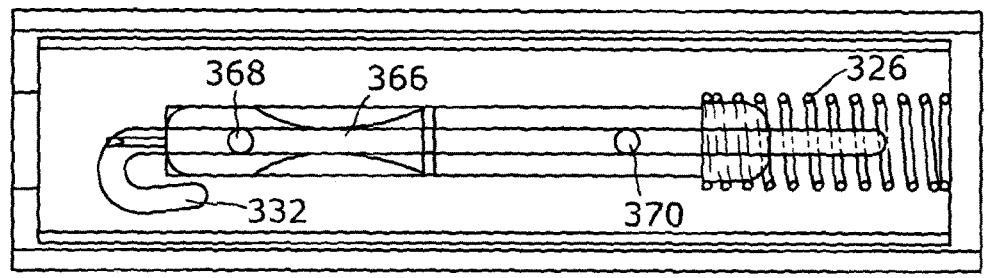

Referring to FIG. 13, in another embodiment the non-return features disclosed above may be incorporated into a linearly moving lancing device to prevent re-cocking. Thus a lancet body 14 constrained to move generally linearly only may be provided with a swing plate 66 pivotally attached to the lancet body at its mid point and carrying a forward peg 68 that runs in a J-profiled track 32 having a return portion with a stop surface at the end. There may also be a rear peg on the plate as shown. The peg or pegs on the plate running in the J-profiled track prevent re-cocking as in the above embodiments, whilst suitable guide pegs 70 on the lancet body run in a linear guide groove 72 constrain it to run linearly.

Instead of the peg or pegs being on a separate element a single peg could be provided on an arm integral with the lancet body and capable of resilient flexing movement. In such a device, as in the operation of FIGS. 9(a) to 9(c) the drive spring will over-extend and then retract so as to cause the lancet tip to momentarily project from the housing to puncture the lancing site, and then return into the housing, but in this arrangement the movement of the lancet body is linear and it is the swing plate peg that follows the J-profile and, after lancing, prevents recocking of the lancet.

Referring now to FIGS. 14(a) to (d) there is shown another embodiment of a lancing device in which a lancet housing 110 with a lancing aperture 122 at its forward end contains a lancet 112 with a tip 116 at its forward end. The lancet is constrained to move linearly within the housing by means of pegs 170 projecting from the lancet body which run in a linear groove 172 provided in an inner side wall of the housing. The lancet is biased forwardly by a longitudinally acting compression coil spring 126 and held in a cocked position as shown in FIG. 14(a) by means of a trigger assembly indicated generally at 120. Pivotally mounted on the side of the lancet body opposite to the pegs 170 is a double-ended swing plate 166 having a peg rotatably received in a socket in the lancet body. The swing plate has two projecting pegs $168^1$ and $168^2$ which run in a profiled branched track 132 in the housing wall. The track 132 comprises a main portion disposed parallel with the linear guide groove 172 but its forward end curves around to one side to provide an overall J-shape. Part way along the main stem portion there is also a loop back or branch portion to the other side.

In operation, upon release of the trigger 120, the lancet body shoots forwardly from the cocked position shown in FIGS. 14(a) and (c), driven by the expanding compression spring 126 until the needle tip 116 momentarily projects through the lancing aperture 122 to prick the skin. As the lancet approaches its forwardmost position, the forward peg $168^1$ enters the curve of the J and so starts to swing the swing plate 166 counter clockwise as viewed in FIGS. 14(c) and (d) so that the pegs $168^1$ and $168^2$ enter the respectively oppositely directed spaced curved portions provided in the track 132. This continues until the spring 126 starts to contract as it rebounds whereupon it pulls the lancet 122 rearwardly and, in so doing, the pegs $168^1$ and $168^2$ pass rearwardly to the blind ends of the branches of the track 132 as the tip is retracted into the housing. In this manner, the lancet is prevented from further rearward movement and so cannot be recocked.

Referring now to the arrangement shown in FIGS. 15(a) to (e) this operates on very similar principles to that shown in FIG. 14, except the swing plate is single armed and carries a single peg 268, and the track 232 has a single branch and is therefore in the form of a simple J shape. The swing plate 266 and the peg 268 operate in the same manner as the forward end of the arm 168 etc in FIG. 14 and so will not be described in detail again. The equivalent components in FIGS. 15(a) to (e) carry the same reference numerals but incremented by 100.

Referring now to the embodiment of FIGS. 16(a) to (d) this is based closely on the arrangement illustrated in FIG. 15 but uses an integral flexural arm or live hinge to allow flexing or pivoting of the arm 366 relative to the lancet body 312 in a manner analogous to that of the pivotal arm 266 and lancet 212 in the arrangement of FIG. 15. As in FIG. 15, the peg 368 that projects from the arm 366 runs in a J shaped track 332. The remaining components of the device to FIGS. 16(a) to (d) are those similar to those of FIGS. 15(a) to (e) and carry equivalent references to their counterparts incremented by 100.

In each of the arrangements of FIGS. 14 to 16, upon firing the lancet, the lancet body shoots forward momentarily projecting the tip and then rebounds thereby pulling a peg or projection into the blind end of a J shaped track portion and preventing recocking of the device.

It will of course be appreciated that the above arrangements could be inverted so one or more of the tracks could be disposed on the body of the lancet with one or more of the pegs disposed on the housing or, on a flexural or pivotal link associated with the housing.

Figure 17:
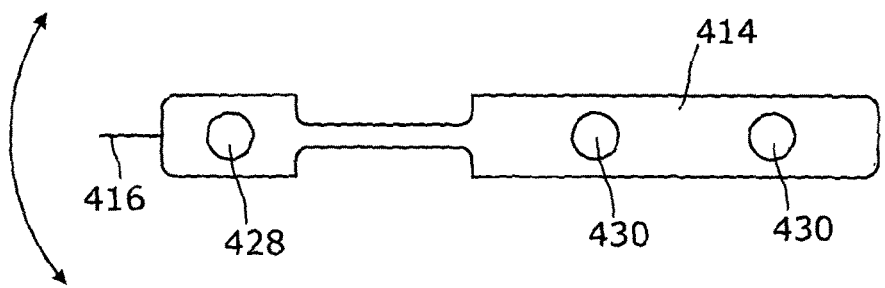
FIG. 17 is a schematic view of an articulated lancet for use in the above embodiments.

As noted above the lancet body may be rigid along its length but, particularly where an extended incision arc is required, the lancet body may comprise articulated front and rear portions, with the rear portion constrained to follow a generally longitudinal path down the housing, whilst the forward portion is pivotally or flexibly attached to the rear portion and is provided with a guide peg that follows the profiled track. An example of such an articulated lancet is shown in FIG. 17. As will be seen the lancet body 414 is necked at a forward region 415, behind the tip 416, to provide a flexural link that enables the tip region to flex or pivot relative to the remainder of the body. The body is provided with pegs 430 that run in a straight part of a guided groove as the lancet moves to its forwardmost position and rebounds, so that the main body movies back and forth in a straight line. A peg 428 on the tip region initially runs in the straight portion but then enters an arcuate portion to cause the tip to describe an arcuate path as it projects from the housing.

In the various embodiments described above the track has been described as J-shaped. It will of course be appreciated that in some applications just the curved end may be used, with the lancet being constrained or otherwise aligned for generally linear movement in some other manner, not requiring the longer limb of the J. Still further, the track may simply be angled relative to the longitudinal axis to provide a lateral deflection, with the track being linear, curved and continuous or interrupted.

The invention claimed is:
1. A lancing device comprising:
a lancet body (14) of elongate form and having a sharp tip (16) at a forward end thereof;
a longitudinally acting drive spring (26) positioned against a rearward end of the lancet body (14) for imparting generally longitudinal movement to said lancet body (14), the drive spring (26) being a longitudinally directed spring strained to apply a forward longitudinally acting force on the rearward end of the lancet body (14);
a housing (10) receiving said lancet body and having an aperture (22) in a forward end thereof,
wherein in use when the device is fired, the lancet body (14) moves longitudinally down the housing (1) under influence of the drive spring (26) applying the forward longitudinally acting force such that the sharp tip (16) of the lancet body projects through the aperture (22); and
an arrangement (28, 30, 32) for controlling movement of the lancet body to cause the sharp tip of the lancet body to deflect laterally during at least part of a period in which the sharp tip of the lancet body (14) projects from said aperture,
wherein in use when the device is fired, i) the drive spring (26) imparts the forward longitudinally acting force to said lancet body (14) to move said lancet body (14) longitudinally down the housing (1) and ii) the arrangement (28, 30, 32) causes a lateral movement of the sharp tip of the lancet body (14) to deflect laterally during at least part of the period in which the sharp tip of the lancet body (14) projects from said aperture,
wherein the arrangement (28, 30, 32) comprises cooperating control surfaces on the lancet body (28, 30) and the housing (32), and
wherein the cooperating control surfaces include a cam surface (32) on the housing and a cam follower (28, 30) on the lancet body, the cam surface (32) having a downstream portion at the forward end of the housing and an upstream portion at the rearward end of the housing, the downstream portion having a U shape open to the rearward end of the housing.

2. The lancing device according to claim 1, wherein the cam follower (28, 30) includes a forward cam follower (28) on the forward end of the lancet body and a rearward cam follower (28) on a rearward part of the lancet body, each of the forward cam follower (28) and the rearward cam follower (30) cooperating with the cam surface (32) throughout at least part of a forward stroke of movement of the lancet body when fired.

3. The lancing device according to claim 1, wherein the downstream portion ($32^3$) is adapted to cause said lateral movement when the sharp tip is exposed.

4. The lancing device according to claim 3, wherein the upstream portion ($32^1$) is generally straight and parallel to a longitudinal axis of the device.

5. The lancing device according to claim 4, wherein an intermediate portion ($32^2$) is provided between the upstream and downstream portions ($32^1$, $32^3$).

6. The lancing device according to claim 5, wherein,
the cam follower (28, 30) on the lancet body includes a forward cam follower (28) on the forward end of the lancet body and a rearward cam follower (28), each of the forward cam follower (28) and the rearward cam follower (30) cooperating with the cam surface (32) throughout at least part of a forward stroke of movement of the lancet body when fired, and
the intermediate portion ($32^2$) is inclined to the longitudinal axis, so that, while the lancet body (14) moves longitudinally down the housing (1) under influence of the drive spring (26), the cam surface deviates firstly in one direction in the intermediate portion, and then in a reverse direction in the downstream portion ($32^3$) so that the forward cam follower (28) moving in the cam surface (32) deflects the sharp tip (16) transversely in one direction as the lancet body moves forwardly within the lancet housing and then deflects the sharp tip (16) in an opposite transverse direction during at least part of the period when the sharp tip is exposed through the aperture (22) of the housing.

7. The lancing device according to claim 3, wherein the downstream portion ($32^3$) is generally curved.

8. The lancing device according to claim 1, wherein the lancing device, when fired, the drive spring (26) urges the lancet body forwards to cause the tip (16) to project through the housing aperture and then to retract back into the housing as the spring rebounds retracting the lancet body with the sharp tip back into the housing, thereby to render the device safe.

9. The lancing device according to claim 8, including a further arrangement adapted to prevent or limit forward movement of the lancet body after the lancet body has been retracted back into the housing.

10. The lancing device according to claim 9, wherein said further arrangement includes a feature on the lancet body that snaps past a feature on the housing.

11. The lancing device according to claim 8, wherein,
the cam surface (32) is adapted to cause said lateral movement when the sharp tip is exposed, and the cam surface (32) further includes an intermediate portion ($32^2$) provided between the upstream and downstream portions ($32^1$, $32^3$),
the cam follower (28, 30) on the lancet body includes a forward cam follower (28) and a rearward cam follower (30) on the lancet body, each of the forward cam follower (28) and the rearward cam follower (30) cooperating with the cam surface (32) throughout at least part of the forward stroke of movement of the lancet body when fired, and
the downstream portion ($32^3$) with the U shape open to the rearward end of the housing (10), has a first limb of the U merging with the upstream portion ($32^2$) or the intermediate portion ($32^1$), whereby when the device is fired, the forward cam follower (28) is driven down said one limb to a base of the U as the lancet body (16) is driven forwardly by the spring (26) and then the forward cam follower (28) is driven backwardly along a second limb of the U when the lancet body is retracted by rebound action of the spring such that the forward cam follower (28) moving in the first limb deflects the sharp tip transversely in one direction and then deflects the sharp tip in an opposite transverse direction.

12. The lancing device according to claim 11, wherein the second limb of the U shaped downstream portion ($32^3$) is blind or has an associated stop surface (33) whereby, following firing, the lancet body (16) is trapped against further rearward movement.

13. The lancing device according to claim 1, wherein the lancet body (16) has a guide element (52) running in a slot or groove (56) in the housing (10) to guide movement of the lancet body.

14. The lancing device according to claim 1, wherein the sharp tip of the lancet body (14) is provided by the sharp forward end of a lancet needle (16) forming part of the lancet body or embedded therein.

15. The lancing device according to claim 14, wherein the needle (16) is of cylindrical form having two machined surfaces (34, 36) defining a cutting edge (38) at a forward end of the needle (16).

16. The lancing device according to claim 15, wherein the lancet needle is provided with a datum feature spaced (40) rearwardly of the cutting edge (38).

17. The lancing device according to claim 1, wherein a resilient element is adapted to be strained between said lancet body and said housing as the lancet body moves forwards within the housing when fired, the resilient element then urging the lancet body to assist said deflection when the lancet body projects through said aperture.

18. The lancing device according to claim 17, wherein said resilient element comprises a spring element formed on said lancet body.

* * * * *